United States Patent
Tedesco et al.

(10) Patent No.: US 9,777,057 B2
(45) Date of Patent: Oct. 3, 2017

(54) ANTIBODIES TO β2-GLYCOPROTEIN I AND THERAPEUTIC USES THEREOF

(71) Applicant: Onconox APS, Copenhagen (DK)

(72) Inventors: Francesco Tedesco, Trieste (IT); Pier Luigi Meroni, Milan (IT); Daniele Sblattero, Trieste (IT)

(73) Assignee: ONCONOX APS, Copenhagen, OT (DK)

( * ) Notice: Subject to any disclaimer, the term of this patent is extended or adjusted under 35 U.S.C. 154(b) by 0 days.

(21) Appl. No.: 14/903,284

(22) PCT Filed: Jul. 7, 2014

(86) PCT No.: PCT/EP2014/064400
§ 371 (c)(1),
(2) Date: Jan. 7, 2016

(87) PCT Pub. No.: WO2015/004038
PCT Pub. Date: Jan. 15, 2015

(65) Prior Publication Data
US 2016/0152696 A1    Jun. 2, 2016

Related U.S. Application Data

(60) Provisional application No. 61/844,505, filed on Jul. 10, 2013.

(51) Int. Cl.
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/33* (2013.01); *C07K 2317/52* (2013.01); *C07K 2317/622* (2013.01); *C07K 2317/64* (2013.01); *C07K 2317/76* (2013.01)

(58) Field of Classification Search
None
See application file for complete search history.

(56) References Cited

U.S. PATENT DOCUMENTS 7,008,623 B1 *  3/2006  Bonnefoy .......... C07K 16/2851
424/143.1

FOREIGN PATENT DOCUMENTS

CN    102816238 A    12/2012
WO    0001729 A2     1/2000

OTHER PUBLICATIONS

Janeway et al., Immunobiology, 3$^{rd}$ edition, 1997, Garland Publishing Inc., pp. 3:1-3:11.*
Rudikoff et al., Proc Natl Acad Sci U S A. Mar. 1982;79(6):1979-83.*
Iverson et al., Proc Natl Acad Sci U S A. Dec. 22, 1998;95(26):15542-6.*
Tedesco, F., Lupus, (Apr. 2010) vol. 19, No. 4, pp. 497-498. Abstract A006.*
Li et al., Autoimmun Rev. Sep. 2003;2(5):229-34.*
Fischetti et al., Blood. Oct. 1, 2005;106(7):2340-6. Epub Jun. 14, 2005.*
Agostinis C. et al., "A human monoclonal antibody against domain I of beta 2-glycoprotein I prevents clotting and fetal loss induced by polyclonal anti-phospholipid antibodies in animal models", Arthritis & Rheumatism, vol. 65, No. Suppl. 10 sp. Iss Si, Oct. 2013, pp. S245.
Di Simone N. et al., "Antiphospholipid antibodies affect human endometrial angiogenesis: protective effect of a synthetic peptide (TIFI) mimicking the phospholipid binding site of [beta](2) glycoprotein 1", American Journal of Reproductive Immunology, Oct. 2013, vol. 70, No. 4, May 7, 2013 pp. 299-308.
International Search Report and Written Opinion of PCT/EP2014/064400 of Nov. 7, 2014.
Pericleous C. et al., "Evaluating the conformation of recombinant domain I of [beta](2)-glycoprotein I and its interaction with human monoclonal antibodies", Molecular Immunology Oct. 2011, pp. 56-63.
Zhu Min, et al., "Characterization of IgG monoclonal anti-cardiolipin/anti-beta2GP1 antibodies from two patients with antiphospholipid syndrome reveals three species of antibodies", British Journal of Haematology, vol. 105, No. 1, Apr. 1999, pp. 102-109.

* cited by examiner

*Primary Examiner* — Michael Szperka
(74) *Attorney, Agent, or Firm* — Silvia Salvadori, P.C.; Silvia Salvadori

(57) ABSTRACT

Human recombinant antibodies or fragments thereof having specificity for the β2-glycoprotein I (β2GPI), pharmaceutical compositions containing same and use thereof in a method for treating or preventing thrombus formation and fetal loss in a patient affected by antiphospholipid syndrome (APS).

10 Claims, 10 Drawing Sheets

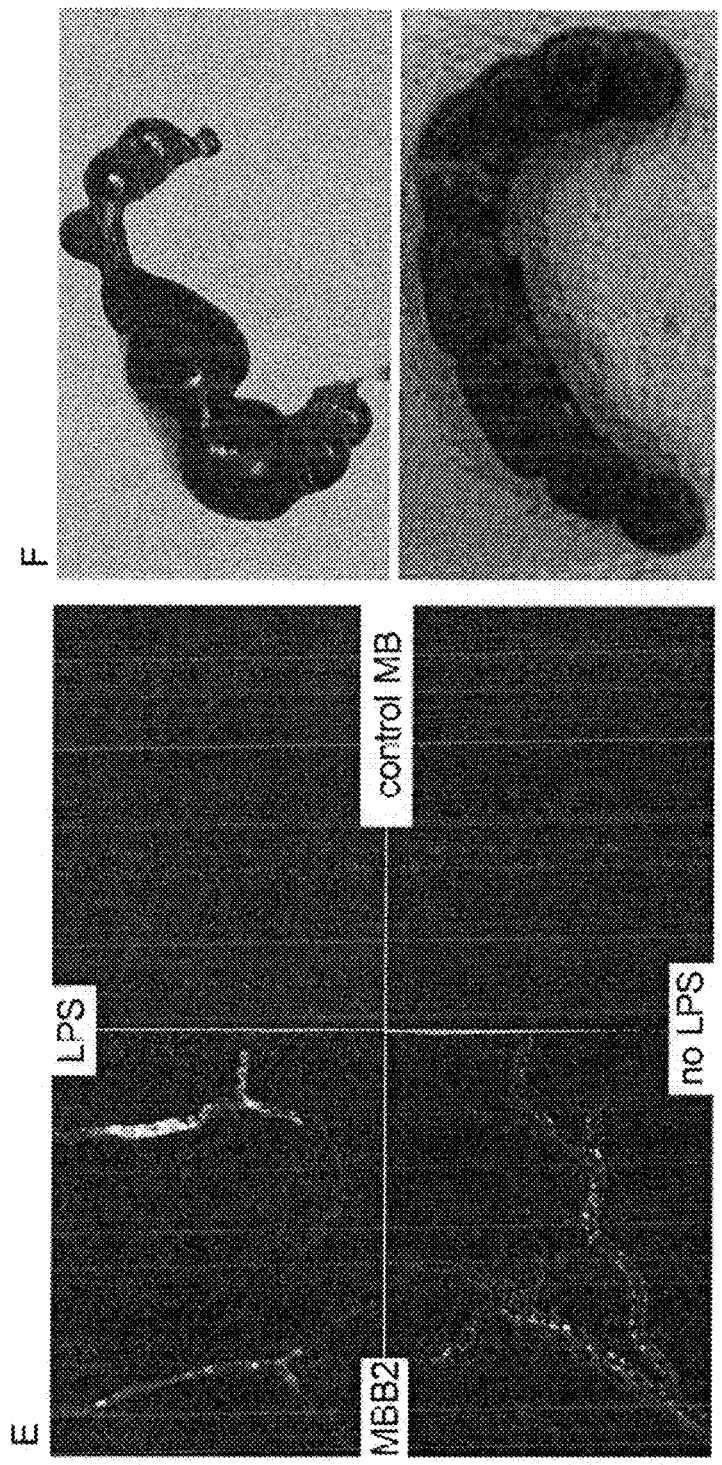
Figure 3 (continue)

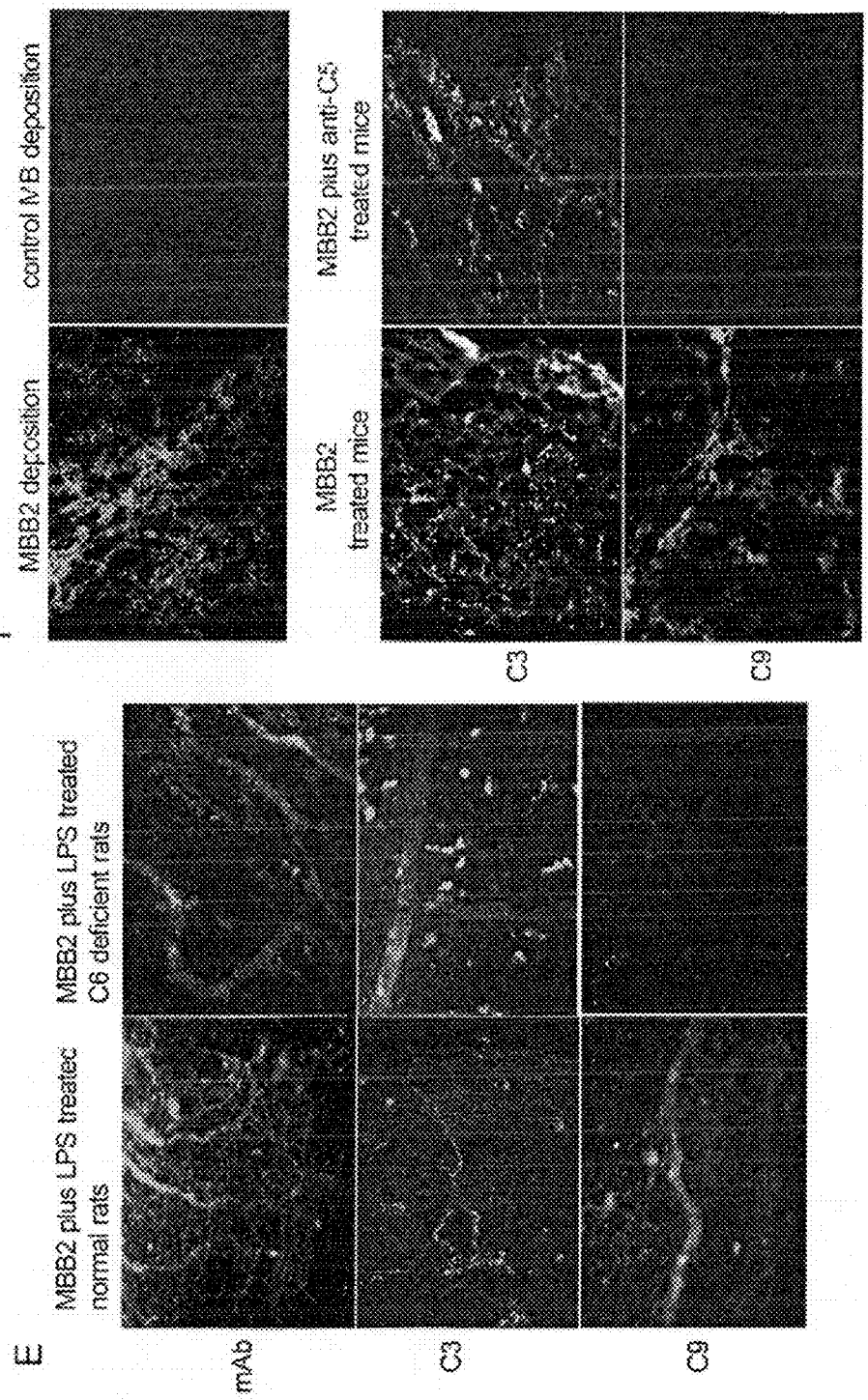
Figure 6 (continue)

SEQUENCE LISTING

<160> NUMBER OF SEQ ID NOS: 9

<210> SEQ ID NO 1
<211> LENGTH: 121
<212> TYPE: PRT
<213> ORGANISM: Homo sapiens

<400> SEQUENCE: 1

Gln Val Gln Leu Gln Glu Ser Gly Gly Gly Leu Val Gln Pro Gly Arg
1               5                   10                  15

Ser Leu Arg Leu Ser Cys Ala Ala Ser Gly Leu Thr Phe Ser Asn His
            20                  25                  30

Gly Met Tyr Trp Val Arg Gln Ala Pro Gly Lys Gly Leu Glu Trp Val
        35                  40                  45

Ala Asp Ile Trp Ser Asp Gly Ser Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp His Tyr Gly Pro Gly Tyr Trp Tyr Phe Asp Leu Trp Gly
            100                 105                 110

Arg Gly Thr Leu Val Thr Val Ser Ser
        115                 120

<210> SEQ ID NO 2
<211> LENGTH: 108
<212> TYPE: PRT
<213> ORGANISM: Homo sapiens

<400> SEQUENCE: 2

Gln Pro Val Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Ser Gly Leu Gln Ser Glu
65                  70                  75                  80

Asp Glu Ala Asp Tyr Phe Cys Ala Ala Trp Asp Asp Ser Leu Ser Gly
                85                  90                  95

Pro Val Phe Gly Gly Gly Thr Lys Leu Thr Val Leu
            100                 105

<210> SEQ ID NO 3
<211> LENGTH: 1485
<212> TYPE: DNA
<213> ORGANISM: Homo sapiens

<400> SEQUENCE: 3
cagcctgtgc tgactcagga ccctgctgtg tctgtggcct tgggacagac agtcagggtc      60
acatgccaag agacagcct cagaagctat tatgcaagt ggtaccagca aaagccagga       120
caggcccctg tacttgtcat ctatggtaaa aacaaccggc cctcagggat cccagaccga     180
ttctctggct ccagctcggg aaacacagct tccttgacca tcagtgggct ccagtccgag     240
gatgaggctg actatttctg tgcagcgtgg gacgacagcc tgagtggtcc ggtattcggc     300
ggagggacca agctgaccgt cctatccgga gggtcgacca acttcgta taatgtatac      360 tatacgaagt tatcctcgag cggtacccag gtgcagctgc aggagtcggg gggaggcttg     420
gtccagcctg ggaggtccct gagactctcc tgtgcagcct ctggactcac cttcagtaat     480

```
catggcatgt actgggtccg ccaggctcca ggcaagggc tggagtgggt ggcagatata    540
tggtctgatg aagtaataa atactatgca gactccgtga agggccgatt caccatctcc    600
agagacaatt ccaagaacac ggtgtatctt caaatgaaca gcctgagagc cgaggacacg    660
gccgtatatt actgtgcgag agatcactat ggtccgggtt actggtactt cgatctctgg    720
ggccgtggaa ccctggtcac cgtctcctca gctagcgaca aaactcacac atgcccaccg    780
tgcccagcac ctgaactcct ggggggaccg tcagtcttcc tcttccccc aaaacccaag     840 gacaccctca tgatctcccg gacccctgag gtcacatgcg tggtggtgga cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc   1020
ctgcaccagg actggctgaa tggcaaggag tacaagtgca aggtctccaa caaagccctc   1080
ccagccccca tcgagaaaac catctccaaa gccaagggc agccccgaga ccacaggtg    1140 tacaccctgc cccatcccg ggaggagatg accaagaacc aggtcagcct gacctgcctg   1200
gtcaaaggct tctatcccag cgacatcgcc gtggagtggg agagcaatgg gcagccggag   1260
aacaactaca agaccacgcc tcccgtgctg gactccgacg gctccttctt cctctatagc   1320
aagctcaccg tggacaagag caggtggcag caggggaacg tcttctcatg ctccgtgatg   1380
catgaggctc tgcacaacca ctacacgcag aagagcctct ccctgtcccc gggtaaaact   1440
agtggcaaac caatcccaaa cccactgctg ggcctggata gtact           1485

<210> SEQ ID NO 4
<211> LENGTH: 363
<212> TYPE: DNA
<213> ORGANISM: Homo sapiens

<400> SEQUENCE: 4
caggtgcagc tgcaggagtc gggggggaggc ttggtccagc ctggggaggtc cctgagactc     60 tcctgtgcag cctctggact caccttcagt aatcatggca tgtactgggt ccgccaggct    120
ccaggcaagg gctggagtg gtggcagat atatggtctg atggaagtaa taaatactat      180
gcagactccg tgaagggccg attcaccatc tccagagaca attccaagaa cacggtgtat    240
cttcaaatga acagcctgag agccgaggac acggccgtat attactgtgc gagagatcac    300
tatggtccgg gttactggta cttcgatctc tggggccgtg gaaccctggt caccgtctcc    360
tca                                                                  363

<210> SEQ ID NO 5
<211> LENGTH: 324
<212> TYPE: DNA
<213> ORGANISM: Homo sapiens

<400> SEQUENCE: 5
cagcctgtgc tgactcagga cctgctgtg tctgtggcct tgggacagac agtcagggtc       60
acatgccaag agacagcct cagaagctat tatgcaagct ggtaccagca gaagccagga    120
caggcccctg tacttgtcat ctatggtaaa aacaaccggc cctcagggat cccagaccga    180
ttctctggct ccagctcggg aaacacagct tccttgacca tcagtgggct ccagtccgag    240
gatgaggctg actatttctg tgcagcgtgg gacgacagcc tgagtggtcc ggtattcggc    300
ggagggacca agctgaccgt ccta                                            324

<210> SEQ ID NO 6
```

```
<211> LENGTH: 495
<212> TYPE: PRT
<213> ORGANISM: Homo sapiens

<400> SEQUENCE: 6

Gln Pro Val Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Ser Gly Leu Gln Ser Glu
65                  70                  75                  80

Asp Glu Ala Asp Tyr Phe Cys Ala Ala Trp Asp Asp Ser Leu Ser Gly
                85                  90                  95

Pro Val Phe Gly Gly Gly Thr Lys Leu Thr Val Leu Ser Gly Gly Ser
            100                 105                 110

Thr Ile Thr Ser Tyr Asn Val Tyr Tyr Thr Lys Leu Ser Ser Ser Gly
        115                 120                 125

Thr Gln Val Gln Leu Gln Glu Ser Gly Gly Gly Leu Val Gln Pro Gly
130                 135                 140

Arg Ser Leu Arg Leu Ser Cys Ala Ala Ser Gly Leu Thr Phe Ser Asn
145                 150                 155                 160

His Gly Met Tyr Trp Val Arg Gln Ala Pro Gly Lys Gly Leu Glu Trp
                165                 170                 175

Val Ala Asp Ile Trp Ser Asp Gly Ser Asn Lys Tyr Tyr Ala Asp Ser
            180                 185                 190

Val Lys Gly Arg Phe Thr Ile Ser Arg Asp Asn Ser Lys Asn Thr Val
        195                 200                 205

Tyr Leu Gln Met Asn Ser Leu Arg Ala Glu Asp Thr Ala Val Tyr Tyr
210                 215                 220

Cys Ala Arg Asp His Tyr Gly Pro Gly Tyr Trp Tyr Phe Asp Leu Trp
225                 230                 235                 240

Gly Arg Gly Thr Leu Val Thr Val Ser Ser Ala Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Thr Cys Leu
```

| | | | | | | | | | | | | | | |
|---|---|---|---|---|---|---|---|---|---|---|---|---|---|---|
| | | 385 | | | 390 | | | 395 | | | 400 | | | |

Val Lys Gly Phe Tyr Pro Ser Asp Ile Ala Val Glu Trp Glu Ser Asn
                      405                      410                      415

Gly Gln Pro Glu Asn Asn Tyr Lys Thr Thr Pro Pro Val Leu Asp Ser
            420                      425                      430

Asp Gly Ser Phe Phe Leu Tyr Ser Lys Leu Thr Val Asp Lys Ser Arg
                435                      440                      445

Trp Gln Gln Gly Asn Val Phe Ser Cys Ser Val Met His Glu Ala Leu
   450                          455                      460

His Asn His Tyr Thr Gln Lys Ser Leu Ser Leu Ser Pro Gly Lys Thr
465                      470                      475                      480

Ser Gly Lys Pro Ile Pro Asn Pro Leu Leu Gly Leu Asp Ser Thr
                485                      490                      495

<210> SEQ ID NO 7
<211> LENGTH: 1173
<212> TYPE: DNA
<213> ORGANISM: Homo sapiens

<400> SEQUENCE: 7

| | | | | | |
|---|---|---|---|---|---|
| cagcctgtgc | tgactcagga | ccctgctgtg | tctgtggcct | gggacagac | agtcagggtc | 60 |
| acatgccaag | agacagcct | cagaagctat | tatgcaagct | ggtaccagca | gaagccagga | 120 |
| caggcccctg | tacttgtcat | ctatggtaaa | acaaccggc | cctcagggat | cccagaccga | 180 |
| ttctctggct | ccagctcggg | aaacacagct | tccttgacca | tcagtgggct | ccagtccgag | 240 |
| gatgaggctg | actatttctg | tgcagcgtgg | gacgacagcc | tgagtggtcc | ggtattcggc | 300 |
| ggagggacca | agctgaccgt | cctatccgga | gggtcgacca | taacttcgta | taatgtatac | 360 |
| tatacgaagt | tatcctcgag | cggtacccag | gtgcagctgc | aggagtcggg | gggaggcttg | 420 |
| gtccagcctg | gggaggtccct | gagactctcc | tgtgcagcct | ctggactcac | cttcagtaat | 480 |
| catggcatgt | actgggtccg | ccaggctcca | ggcaaggggc | tggagtgggt | ggcagatata | 540 |
| tggtctgatg | gaagtaataa | atactatgca | gactccgtga | agggccgatt | caccatctcc | 600 |
| agagacaatt | ccaagaacac | ggtgtatctt | caaatgaaca | gcctgagagc | cgaggacacg | 660 |
| gccgtatatt | actgtgcgag | agatcactat | ggtccgggtt | actggtactt | cgatctctgg | 720 |
| ggccgtggaa | ccctggtcac | cgtctcctca | gctagccaca | catgcccacc | gtgcggtgga | 780 |
| ggcggttcag | gcggaggtgg | ctctgggcag | ccccgagaac | acaggtgta | caccctgccc | 840 |
| ccatcccggg | aggagatgac | caagaaccag | gtcagcctga | cctgcctggt | caaaggcttc | 900 |
| tatcccagcg | acatcgccgt | ggagtgggag | agcaatgggc | agccggagaa | caactacaag | 960 |
| accacgcctc | ccgtgctgga | ctccgacggc | tccttcttcc | tctatagcaa | gctcaccgtg | 1020 |
| gacaagagca | ggtggcagca | ggggaacgtc | ttctcatgct | ccgtgatgca | tgaggctctg | 1080 |
| cacaaccact | acacgcagaa | gagcctctcc | ctgtccccgg | gtaaaactag | tggcaaacca | 1140 |
| atcccaaacc | cactgctggg | cctggatagt | act | | | 1173 |

<210> SEQ ID NO 8
<211> LENGTH: 80
<212> TYPE: PRT
<213> ORGANISM: Homo sapiens

<400> SEQUENCE: 8

Ala Cys Gly Thr Gly Cys Thr Ala Gly Cys Cys Ala Cys Ala Cys Ala
1                  5                          10                          15

```
Thr Gly Cys Cys Cys Ala Cys Cys Gly Thr Gly Cys Gly Gly Thr Gly
                20                  25                  30

Gly Ala Gly Gly Cys Gly Gly Thr Thr Cys Ala Gly Gly Cys Gly Gly
        35                  40                  45

Ala Gly Gly Thr Gly Gly Cys Thr Cys Thr Gly Gly Gly Cys Ala Gly
        50                  55                  60

Cys Cys Cys Cys Gly Ala Gly Ala Ala Cys Cys Ala Cys Ala Gly Gly
65              70                  75                  80

<210> SEQ ID NO 9
<211> LENGTH: 43
<212> TYPE: PRT
<213> ORGANISM: Homo sapiens

<400> SEQUENCE: 9

Thr Gly Cys Thr Ala Ala Gly Cys Thr Thr Thr Ala Ala Gly Thr
1               5                  10                  15

Ala Cys Thr Ala Thr Cys Cys Ala Gly Gly Cys Cys Cys Ala Gly Cys
                20                  25                  30

Ala Gly Thr Gly Gly Gly Thr Thr Thr Gly Gly
        35                  40
```

ANTIBODIES TO β2-GLYCOPROTEIN I AND THERAPEUTIC USES THEREOF

This application is a U.S. national stage of PCT/EP2014/064400 filed on 7 Jul. 2014, which claims priority to and the benefit of U.S. Provisional Application No. 61/844,505 filed on 10 Jul. 2013, the contents of which are incorporated herein by reference in their entireties.

The present invention provides human recombinant antibodies or fragments thereof for the treatment of patients affected by antiphospholipid syndrome (APS). More specifically the invention provides a recombinant human antibody having specificity for the β2-glycoprotein I (β2GPI), wherein said antibody recognizes a region corresponding to the DI domain of the β2-glycoprotein I (β2GPI) and it is rendered unable to fix complement, and a method for treating or preventing thrombus formation, vessel occlusion or fetal loss in a patient affected by antiphospholipid syndrome (APS), which comprises administering to a patient in need thereof said antibody or antibody fragment.

BACKGROUND OF THE INVENTION

Antiphospholipid syndrome (APS) is a systemic autoimmune disease characterized by recurrent arterial and/or venous thrombosis and pregnancy morbidities in the persistent presence of autoantibodies against phospholipid binding proteins (aPL). The syndrome occurs either as primary or secondary disorder to other autoimmune diseases such as systemic lupus erythematosus. APS has a strong social and economical impact affecting mainly young people and inducing disability as a consequence of stroke or myocardial infarction[1]. A few patients manifest a life-threatening form of APS characterized by thrombotic occlusion of small vessels in different organs developing in a short period of time and leading to multi-organ failure[2]. Pregnancy morbidity includes recurrent early and late miscarriages, intra-uterine growth restriction, prematurity, and pre-eclampsia with high social and economical costs[1,3].

Data obtained from clinical studies and animal models argue for the involvement of antibodies in thrombus formation and miscarriage in APS. Although several PL-binding proteins have been identified as potential targets of aPL, there is strong evidence that β2-glycoprotein I (β2GPI) is the most relevant target antigen[4-7].

We have recently reported a significant increase in fetal loss in pregnant mice immunized with human β2GPI following injection of fluorescent-labeled purified protein that binds selectively at fetal implantation sites[8]. We also found that removal of antibodies to β2GPI from aPL-IgG purified from APS patients by affinity chromatography significantly reduced their thrombotic effect in the rat mesenteric microcirculation[9].

Although antibodies display a modest reactivity with the molecule in the fluid phase, it is widely accepted that they bind preferentially to β2GPI present on the membrane of different cell types including endothelial cells, platelets, monocytes and trophoblast plays a major pathogenic role[10]. In particular, pathogenic aPL have recently been suggested to recognize an conformational immunodominant epitope formed in Domain I (DI) of β2GPI[7]. The mechanisms linking aPL to blood clotting and fetal loss encompass inhibition of natural anticoagulants and fibrinolysis, activation of endothelial cells, platelets and monocytes resulting in expression of adhesion molecules and release of tissue factor, inhibition of syncytium-trophoblast differentiation and promotion of decidual inflammation[10]. However, these aPL-mediated effects have been proposed mainly on the basis of in vitro data, but the in vivo relevance of these observations remains to be fully established.

Compelling evidence for the critical role played by complement in APS has been obtained in animal models starting from the finding by Holers and colleagues[11] that mice deficient in C3 or treated with an inhibitor of the C3 convertase are protected from aPL-mediated fetal resorption and growth retardation. Subsequent studies led to the identification of the activation products of the terminal pathway C5a and MAC as mediators of fetal loss and thrombus formation using animals with selective complement deficiencies or treated with specific inhibitors[12]. Although most of these observations were made with aPL of undefined specificity, the role of complement in inducing aPL-mediated blood clotting and fetal resorption has also been confirmed using specific antibodies to β2GPI[8,9].

In recent years major efforts have been made to control the pathologic effects of aPL preventing the development of thrombi and miscarriages. Anticoagulants such as heparin or warfarin are currently used to prevent vascular thrombi and the combination of low-dose aspirin and low molecular weight heparin represents the first-line treatment for obstetric complications of APS. However, despite the success of these therapeutic approaches in several patients with APS, there is still a good proportion of patients varying between 20 and 30% who do no benefit from these treatments[13-14,15].

DESCRIPTION OF THE INVENTION

The invention provides antibodies or antibody fragments to the β2-glycoprotein I (β2GPI) and their use in a method of treating or preventing thrombus formation and fetal loss in a patient affected by antiphospholipid syndrome (APS).

The human recombinant antibodies or fragments according to the invention recognize a region corresponding to the DI domain of β2GPI (see bibliographic references 40 and 41 for a definition of the DI domain) and are rendered unable to activate complement following to β2GPI binding.

In one embodiment, the antibody or fragment thereof is able to displace patient's autoantibodies bound to β2GPI in in vitro competitive binding assays.

In another embodiment, the antibody or fragment thereof contains VH and VL chains having the sequences SEQ ID NO: 1 and SEQ ID NO:2, respectively, or sequences identical to SEQ ID NO: 1 or SEQ ID NO:2 by at least 95%.

In another embodiment, said VH and VL chains are encoded by the polynucleotide sequences identified by SEQ ID NOs: 4 and 5, respectively.

In a preferred embodiment, said antibody is a human immunoglobulin IgG.

In a another embodiment, the antibody fragment is a single-chain antibody fragment (scFv), wherein the VL and VH are operatively attached by a linker.

In a yet further embodiment, the antibody fragment is a scFv-Fc which further comprises an amino acid sequence of an immunoglobulin heavy chain constant region or a subdomain of an immunoglobulin heavy chain constant region, wherein said immunoglobulin heavy chain constant region is preferably selected from the human IgG heavy chain.

In a preferred embodiment, the antibody according to the invention or a fragment thereof, particularly the scFv-Fc fragment, is rendered unable to fix complement by deletion of the IgG CH2 domain.

In another preferred embodiment, the scFv and scFv-Fc fragments are encoded by the polynucleotides SEQ ID NO:7 and SEQ ID NO:3, respectively. The corresponding amino acid sequence of the scFv-Fc fragment is identified by SEQ ID NO: 6.

The antibody or fragment thereof according to the invention may further comprise a peptide tag positioned at the C-terminus, wherein said tag does not alter the binding specificity to the β2GPI of said antibody.

Another object of the present invention is a pharmaceutical composition containing, as the active ingredient, the recombinant antibody or fragment thereof as herein defined and a pharmaceutically acceptable carrier.

DETAILED DESCRIPTION OF THE INVENTION

Isolation and Characterization of Anti-human β2GPI Recombinant Antibody.

Screening of human phage display library against human β2GPI allowed us to select a specific scFv that was further engineered into the say-Fe format (MBB2) to contain the hinge region, the CH2 and CH3 domains of human IgG1. Further analysis of MBB2 binding to immobilized β2GPI by ELISA revealed a strong reactivity of the antibody that was still able to detect the target antigen at a concentration of 20 ng/ml (FIG. 1A) and a modest interaction with soluble β2GPI (FIG. 2). MBB2 did not react with solid-phase bound prothrombin. Because our aim was to use the scFv-Fc in animal models, the antibody was also tested for its ability to recognize mouse β2GPI and proved to react with the murine molecule equally well as with the human counterpart suggesting the recognition of a shared epitope (FIG. 1A). The reactivity of MBB2 with β2GPI from other animals species was also evaluated using the conventional anticardiolipin antibody assay in which the cardiolipin-coated plates are treated with blocking buffer containing serum from several animals. The results presented in FIG. 4 show that the antibody reacts to various degrees with cardiolipin-bound β2GPI from several species including rat, mouse, pig, goat and fetal calf. Recombinant single domains of the β2GPI protein were then used to identify the target epitope of the MBB2, and testing four out five domains we found that the antibody binds to the DI domain (FIG. 1B). Binding of MBB2 to DI was subsequently confirmed using solid-phase bound recombinant DI as described by Ioannou et al.[16].

To determine if MBB2 interacts with cell-bound β2GPI, HUVECs and BeWo were first exposed to purified β2GPI to allow surface binding of the protein and then incubated with the scFv-Fc. As shown in FIGS. 1C and D, MBB2, unlike the unrelated antibody, was able to bind to the two cell types loaded with β2GPI. The modest signal observed on BeWo with the highest concentration of the control antibody is compatible with the expression of IgG receptor on these cells[17].

In vivo Effect of MBB2 on Thrombus Formation and Fetal Loss.

Having found that MBB2 interacts with D1 of β2GPI, we sought to investigate the ability of the antibody to cause blood clots and fetal loss in animal models in view of the clinical relevance of antibodies with this specificity in APS patients. To this end, the antibody was injected in rats primed with LPS and its procoagulant effect was monitored in mesenteric microvessels by intravital microscopy. As shown in FIG. 3A, MBB2 induced clot formation that followed a biphasic pattern with an early phase characterized by platelet-leukocyte microaggregates already visible 10 min after antibody infusion. The transient vessel occlusion caused by these aggregates was followed by a second phase characterized by a progressive increase in thrombus size resulting in permanent occlusion of the blood vessels (FIGS. 3A and B). MBB2 injected into unprimed rats caused small leukocyte-platelet conjugates that disappeared after 60 minutes, while the control antibody was completely ineffective (FIGS. 3A and B).

In a second set of experiments we searched for the effect of MBB2 on pregnancy outcome in mice. A single injection of 10 µg of antibody was sufficient to induce a significant rate of fetal resorption with a mean value of 60%, which was significantly higher than the 10% value observed in animals treated with a similar amount of control scFv-Fc. Likewise, the anti-β2GPI antibody was found to affect fetal growth causing a substantial decrease in fetal weight (FIG. 3C-D).

Complement is Required for the in vivo Effect of MBB2.

To investigate the contribution of complement to the pathogenic effect of MBB2, we first analysed the ability of scFv-Fc bound to immobilized β2GPI to activate complement in the presence of NHS as a source of complement. MBB2 was found to trigger the classical pathway as suggested by the binding of C1q and C4 and to promote the assembly of the terminal complex revealed by the deposition of C9 (FIG. 5). The role of the effector phase of complement activation in the development of thrombi induced by MBB2 was evaluated in C6 deficient rats primed with LPS. The antibody had a negligible procoagulant effect in these rats and analysis of the mesenteric vessels revealed deposits of IgG and C3 in the absence of C9 (FIG. 6A, E). The contribution of complement to MBB2-induced fetal loss was analysed in pregnant mice that received C5 neutralizing antibody prior to administration of the anti-β2GPI scFv-Fc. This treatment resulted in inhibition of C9 deposition at implantation sites associated with a significant decrease in fetal loss and increase in fetal weight (FIG. 6 C-D).

Failure of Non Complement Fixing Antibody to β2GPI to Induce in vivo Effect.

Since the CH2 domain of IgG1 contains the binding site for C1q, we generated a modified version of scFv-Fc MBB2 lacking this domain (MBB2ΔCH2) with the aim to further confirm the role of complement in mediating the pathogenic effect of the parent antibody. The results of ELISA presented in FIG. 7A show that MBB2ΔCH2 interacts with β2GPI equally well as MBB2, but, once bound, is unable to activate complement (FIG. 7B). The modified molecule injected into normal rats pretreated with LPS had negligible procoagulant activity with a pattern of prothrombotic effect which resembles that observed in C6 deficient rats, emphasizing the important contribution of complement activation to the thrombotic events (FIG. 7C). Likewise, MBB2ΔCH2 did not affect pregnancy outcome in terms of fetal weight and fetal loss, which instead were severely compromised by MBB2 (FIG. 7E).

MBB2ΔCH2 Prevents the in vivo Effect Induced by Patients' Igs.

The finding that CH2-deleted antibody fails to activate complement despite the strong interaction with immobilized β2GPI led us to consider the possibility that MBB2ΔCH2 may compete with the antibodies to β2GPI from APS patients, thus preventing their pathogenic effect. To this purpose, the procoagulant activity of patients' IgG in rats primed with LPS was compared with that of a mixture of MBB2ΔCH2 and IgG anti-β2GPI. As shown in FIG. 8A-B, the CH2-deleted antibody was able to !educe thrombus formation and vessel occlusion to levels previously obtained with control IgG[9]. The difference in thrombus formation and vessel occlusion between rats receiving IgG aPL+ alone and the animal receiving both IgG aPL+ and MBB2ΔCH2 reached statistical significance after 45 min from infusion. The same molecule administered to pregnant mice was found to significantly reduce fetal death induced by anti-β2GPI IgG from APS patients (FIG. 8C). We were unable to evaluate the beneficial effect of the antibody on fetal weight because this clinical parameter was unaffected by the injection of IgG from patients evaluated in the present investigation.

The use of MBB2ΔCH2 as a therapeutic agent to prevent APL-mediated fetal loss should take into account the clinical observation that APL circulate in blood at the time of embryo implantation when β2GPI is detected on the surface of trophoblast and decidual endothelial cells[8]. This suggests that MBB2ΔCH2 ought to displace antibodies already bound to β2GPI to exert its beneficial effect in patients with APS. To address this issue, immobilized β2GPI were first incubated with patients' IgG for 30 min and subsequently exposed to MBB2ΔCH2. The residual APL still bound to β2GPI was measured using a secondary antibody directed against the CH2 domain of IgG that recognized the patients' antibodies while failing to reveal the CH2 deleted antibody. The results presented in FIG. 8C show that the mutant antibody was able to remove approximately 40-50% patients' IgG. Failure to displace the totality of bound antibodies may be explained by the fact that the polyclonal antibodies circulating in APS patients are probably directed against other epitopes of β2GPI.

Materials and Methods

Purification and Characterization of Human and Murine β2GPI.

β2GPI was purified from pooled human sera obtained from blood donors and mouse serum by perchloric acid treatment followed by affinity purification on Heparin column (HiTrap Heparin HP, GE Healthcare, Milan, Italy) and by ion-exchange chromatography (Resource-S, GE Healthcare). Radial Immunodiffusion was used to identify β2GPI, that was further analysed for purity by SDS-PAGE and Coomassie Blue staining and tested for aPL cofactor activity by ELISA[29].

Full length cDNA clone of human b2GPI[38] cloned into pBacPAK9[39] was used for the construction of the individual domains I, II, IV and V of b2-GPI[40]. A recombinant domain 1 (D1) was also produced using a synthetic DI gene obtained employing a computer programme called Juniper. The gene was cloned into the expression plasmid pET(26b) and expressed in BL21(DE3) *Escherichia coli* (*E. coli*)[41].

Recombinant Antibodies.

The phage display Ab library used for selection was derived from peripheral blood lymphocytes obtained from healthy donors and was previously described[30]. Selection was performed in 96 well plates coated with β2GPI (see below for experimental details) by overnight incubation at 4° C. as previously reported[30]. The panning procedure was repeated twice. After selection 96 random clones were selected and the phages from single colonies were grown in 96-well plates. A positive clone (B2) was identified by phage ELISA and the V genes was sequenced and the VH and VL families, as well as the gene segments used, were assessed by screening using the IMGT/V-QUEST tool in the-IMGT®, the ImMunoGeneTics information system® imgt.cines.fr.

Cloning and Purification of Recombinant Antibodies

The positive scFv B2 was converted into a human scFv-Fc format (MBB2) by subcloning it into the pMB-SV5[31] vector containing the human IgG1 Hinge-CH2-CII3 domain. A similar procedure was followed to generate a mouse scFv-Fc containing TSA 12/22 (Adienne, Pharma & Biotech)[32] anti C5 antibody (MBC5) and anti-human CD20 used as a control MB. A CH2-deleted version of the scFv-Fc (ΔCH2) was created according to[33]. To this aim human IgG1 CH3-SV5 region was amplified with primers Hu_CH3_sense

5'ACGTGCTAGCCACACATGCCCACCGTGCGGTGGAGGCGGTTCAGGCGG

AGGTGGCTCTGGGCAGCCCCGAGAACCACAGG3', SEQ ID NO: 8, and Hu$_{13}$CH3 anti

TGCTAAGCTTTTAAGTACTATCCAGGCCCAGCAGTGGGTTTGG, SEQ ID NO: 9.

PCR fragment was cut with NheI and HindIII and cloned into B2 containing PMB-SV5 vector cut with the same enzymes creating a pMB ΔCH2 vector.

All recombinant antibodies (MBB2, MBB2ΔCH2, MBCS and control MB) were finally subcloned into pUCOE vector[34] for expression. Stable transfected CHO-s cell lines were obtained by selection with Hygromic B (500 μg/ml, Invitrogen). Large scale production of both scFv-Fc fusion were carried out by culturing stably selected cell clones in serum-free CHO-SFM-II medium, supplemented with L-glutamine, antibiotics and Hygromicin B in the disposable CELLine System bioreactor (BD Biosciences), following the manufacturer's instructions. scFv-Fc were purified from at least 40 ml of cell culture supernatant by using a HiTrap protein G column (GE Healthcare) affinity column chromatography on the AKTAprime low-pressure chromatographic system (GE Healthcare, Little Chalfont, England). After elution, the preparations of purified scFv-Fc were dialyzed in BupHTM Phospate buffer (Thermo Scientific, Rockford, Ill.), aliquoted and stored at −80° C.

Sera

Sera were obtained from patients with a history of arterial or venous thrombosis or both and contained medium-high titer of anti-β2GPI antibodies. A pool of fresh sera from 10 blood donors was used as a source of complement. Serum samples were also collected from various animals species including mouse, rat, goat, pigs and fetal calf. IgG were purified from patient sera on a HiTrap Protein G column (Pharmacia, Milan, Italy).

Antibody Binding Assays

The interaction of antibodies with β2GPI was measured by ELISA using γ irradiated polystyrene plates (Maxi-Sorp Nunc-Immunoplates; VWR International) coated with purified human or mouse β2GPI (10 μg/ml) in bicarbonate buffer overnight. After blocking with 1% BSA (Sigma-Aldrich), serial dilutions of antibodies were added to the plates and incubated for 90 min at room temperature (RT). The bound antibodies were revealed by alkaline phosphatase (AP)-conjugated anti-human IgG (Sigma-Aldrich) diluted 1:4,000 and the reaction was developed using p-nitrophenyl phosphate (PNPP) as substrate (Sigma-Aldrich) and read at 405 nm.

A similar approach was followed to investigate the domain specificity of the anti-β2GPI scFv-Fc using recombinant domains kindly provided by Dr. P. G. De Groot (Amsterdam, NL).

Anticardiolipin antibodies were detected as described by Tincani et al[35] with the only modifications that solid-phase bound cardiolipin was exposed to 10% sera from various animals followed by incubation with MBB2 or control MB (1 μg/ml). The bound antibodies was detected as indicated above.

Anti-prothrombin antibodies were revealed using the semi-quantitative QUANTA Lite® aPS/PT IgG and IgM (NOVA Diagnostics) that detects antibodies against phosphatidylserine/prothrombin complex.

Displacement of Patients' Antibody Bound to β2GPI by MBB2ΔCH2

Human β2GPI (10 μg/mL) immobilized on γ-irradiated polystyrene plates was first exposed to patient's serum (1:200) for 30 min at RT followed by incubation with MBB2ΔCH2 (2 μg/100 μl) for 30 min at RT. The amount of residual patient antibody bound to β2GPI was measured by ELISA using a murine monoclonal IgG (Clone MK1A6 AbD Serolec Raleigh USA; 1:1,000) that recognizes the CH2 domain present in the patient's antibody but absent in MBB2ΔCH2 and detected by incubation with 1:10,000 AP-conjugated goat anti-mouse IgG (Sigma-Aldrich) for 60 min at RT.

Binding of MBB2 to Cell-Surface β2GPI

HUVECs and the trophoblast cell line BeWo coated with β2GPI were used as cell targets to test the reactivity of the antibody with the cell-bound molecule. HUVECs were isolated and cultured as previously published[36]. BeWo cells (European Collection of Cell Cultures, ECACC, Salisbury, UK) were grown at 37° C. and 95% air/5% $CO_2$ in RPMI medium 1640 (Gibco, Tnvitrogen) supplemented with 10% FCS (Gibco, Invitrogen).

Binding of MBB2 was assessed on cells grown to confluence in 96-well tissue culture plates (Costar, Milan, Italy) and exposed to purified human β2GPI (5 μg/ml) or 20% FCS for 90 min at 37° C. and 95% air/5% $CO_2$. The cells were then incubated with 100 μl of increasing concentrations of antibody for 1 h at RT followed by (1:4,000) AP- or (1:4,000) Horseradish Peroxidase (HRP)-conjugated goat anti human IgG (Sigma-Aldrich) for HUVEC and BeWo respectively. The enzymatic reaction was developed using PNPP or 3,3',5,5'-Tetramethylbenzidine (TMB) both from Sigma-Aldrich as substrate and read at 405 or 450 nm with a Titertek Multiskan ELISA reader (Flow Labs, Milano, Italy).

Evaluation of Complement Activation

The ability of bound seFv-Fc to trigger the classical pathway of complement activation was tested coating γ-irradiated polystyrene plates with human β2GPI (10 μg/mL) followed by incubation with MBB2 (10 μg/mL) for 90 min at RT. The β2GPI-bound antibody was then exposed to 100 μl of 1:100 AB+ fresh serum for 30 min at 37° C. Deposition of C1q and C4 was detected using 1:8,000 goat anti-human C1q or C4 purchased from Quidel (M-Medical, Milan, Italy). Binding of C9 was revealed using the murine monoclonal antibody aE11 to C9 neoantigen, (1:1,000) kindly provided by Prof. T. E. Mollnes (Oslo, Norway). AP-conjugated anti-goat IgG (1:4,000) or anti-mouse IgG (1:10,000) both from Sigma-Aldrich were employed as secondary antibodies. The enzymatic reaction was developed using PNPP as substrate and read at 405 nm.

Animals

Male rats (270 300 g) were used for the in vivo experiments. Wistar rats were obtained from a local colony kept in the University Animal House. C6+/+ PVG rats were purchased from Harlan Italy (San Pietro al Natisone, Italy), and C6−/− PVG rats were from a previously reported rat colony[37] established in our Animal House. BALB/c mice were purchased from Harlan Italy (San Pietro al Natisone, Italy).

All the experimental procedures were performed in compliance with the guidelines of European (86/609/EEC) and the Italian (D.L.116/92) laws and approved by the Italian Ministry of University and Research as well as by the Administration of the University Animal House.

Rat Model of Thrombosis

Antibody-induced thrombus formation was evaluated in rats as previously described in details[9]. Briefly, the animals received intraperitoneal injections of LPS from *Escherichia coli* O55:B5 (2.5 mg/kg body weight; Sigma-Aldrich) or sterile saline, as a control, and 3 h later were anesthetized with sodium thiobarbital (Inactin; 80 mg/kg). The fluorescent vital dye Rhodamine 6G (Sigma-Aldrich), which stains leukocytes and platelets, was infused slowly into the femoral vein at the concentration of 0.025 mg/kg/min and at a rate of 0.25 ml/h 30 min prior to 30-min infusion of scFv-Fc (1 mg/ml saline) or purified IgG from APS patients (10 mg/ml saline) into the carotid artery. The ability of MBB2ΔCH2 to prevent APL-induced thrombus formation was investigated injecting the CH2-deleted scFv-Fc (2 mg/ml saline/30 min) followed by 30-min infusion of patient IgG (10 mg/ml saline).

At least 3 microvascular areas containing arterioles, capillaries, and postcapillary venules were analyzed for the formation of fluorescent aggregates of leukocytes and platelets that partially or completely occluded the vessels. The results are expressed as a ratio between the number of thrombi and the total number of microvessels examined and also as percentage of occluded microvessels.

Analysis of Pregnancy Outcome.

Female BALB/c mice (6-8 wks of age) were housed with adult stud males at a ratio 3:1 and allowed to mate naturally. Day 0 of pregnancy is defined as the day on which a vaginal plug is found. The pro-abortive effect of antibodies was evaluated in mice that received tail vein infusion of either scFv-Fc (10 μg/100 μl saline/mouse) or patients' IgG (50 μg/100 μl saline/mouse) on day 0 and were sacrificed on day 15. Complement depletion was achieved in mice by intraperitoneal injection of neutralizing MBC5 (100 μg/400 μl saline/mouse) three times a week. Resorbed fetuses were identified by their small size and necrotic or hemorrhagic appearance compared with normal embryos. The results are presented as percentage of fetal loss. The weight of uterus and individual fetuses with respective placentae were also recorded. In experiments aimed to evaluate the control of APL-induced fetal loss by MBB2ΔCH2, female mice received i.v. patients' IgG (50 μg/100 μl saline/ mouse) on day 0 of pregnancy and intraperitoneal injections of MBB2ΔCH2 (50 μg/200 μl saline/mouse) on days 0, 5. and 10. Resorbed fetuses were identified and counted. The results are presented as percentage of fetal loss and weight of uterus and individual fetuses.

Immunofluorescence Analysis

The mesenteric tissue were harvested from rats killed at the end of in vivo experiment after intracarotid infusion of sterile saline to remove blood as previously described[9]. The dissected tissue was cut into small pieces and stretched on polylysine-treated glass slides (BDH Laboratory Supplies, Poole, United Kingdom).

Sections (7 μm) of snap-frozen samples of mouse placentae embedded in OCT medium (Diagnostic Division, Miles, Inc.) were used. Tissue deposition of mouse C3 and C9 was analysed by indirect immunofluorescence using 1:400 goat anti-mouse C3 (MP Cappel, Solon, USA), and 1:200 rabbit anti-mouse C9 (a kind gift of Prof. M. D Daha, Leiden, N L) followed by FITC-conjugated secondary antibodies (Dako, Milan, Italy). The slides were examined under a fluorescence Leica DM2000 microscope (Leica, Milan, Italy).

Statistical Analysis

Statistical analyses were performed using GraphPad Prism 5.0 for Windows. The data of fetal resorption and vessels occlusion and the ELISA results were analyzed with the Mann-Whitney test. Fetal weights was analyzed using the t-Student test. Data were expressed as mean±standard deviation and a P-value less than 0.05 was considered statistically significant.

Figure 1:
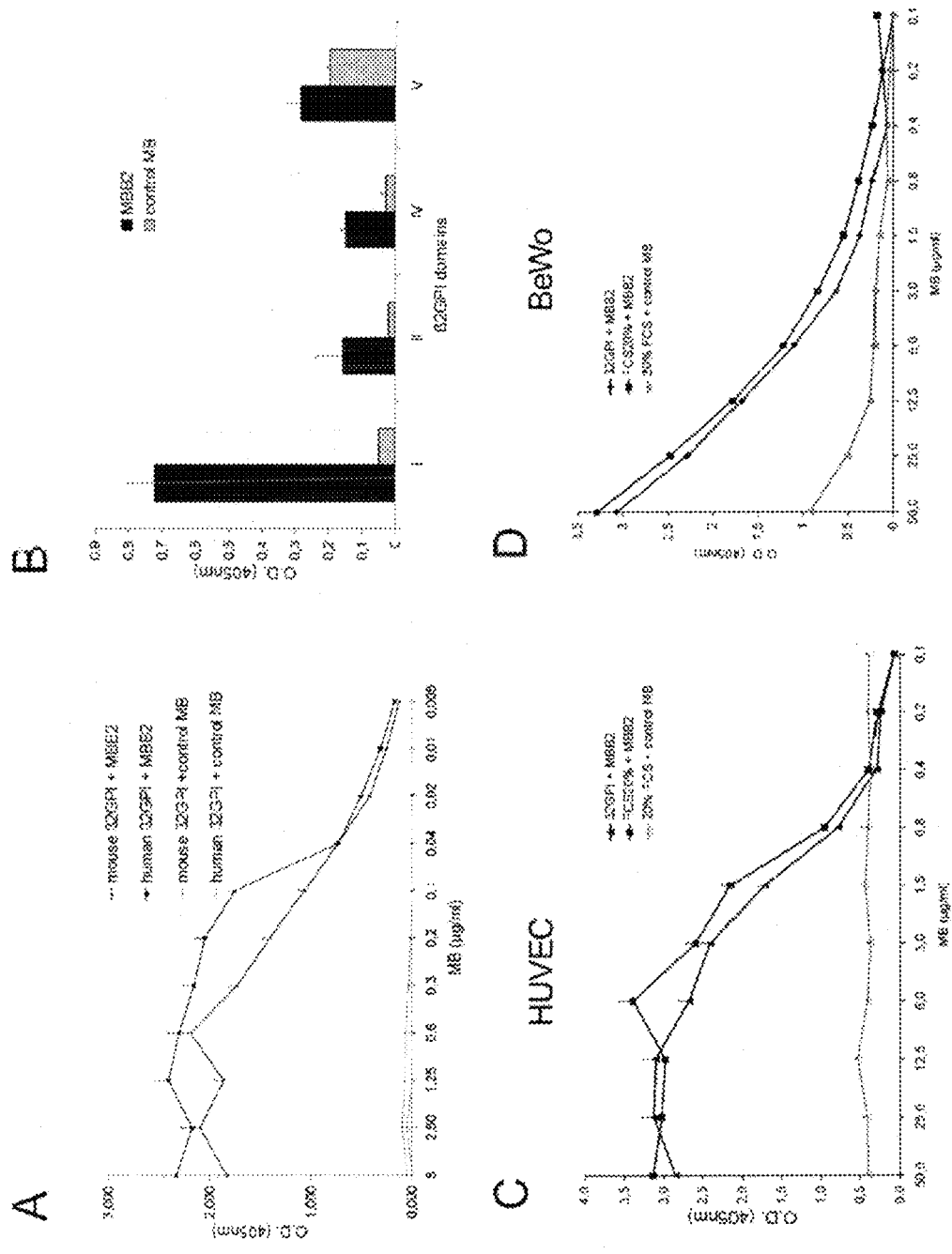
FIG. 1. Analysis of MBB2 binding to purified β2GPI. (A) Human or mouse β2GPI (10 µg/mL) immobilized on γ-irradiated polystyrene plates were incubated with different concentrations of MBB2 or control MB and the bound scFv-Fc was revealed by ELISA. (B) Binding of MBB2 to human β2GPI domains (10 µg/mL) was analyzed as reported in A. The graphs in C and D show binding of MBB2 or control MB to HUVEC or BeWo grown to confluence in 96-well tissue culture plates. The cells were incubated with β2GPI (5 µg/ml) or 20% FCS prior to exposure to the scFv-Fc. Bound antibodies were revealed by ELISA. The results are expressed as mean± SD of experiments run in triplicates.
Figure 2:
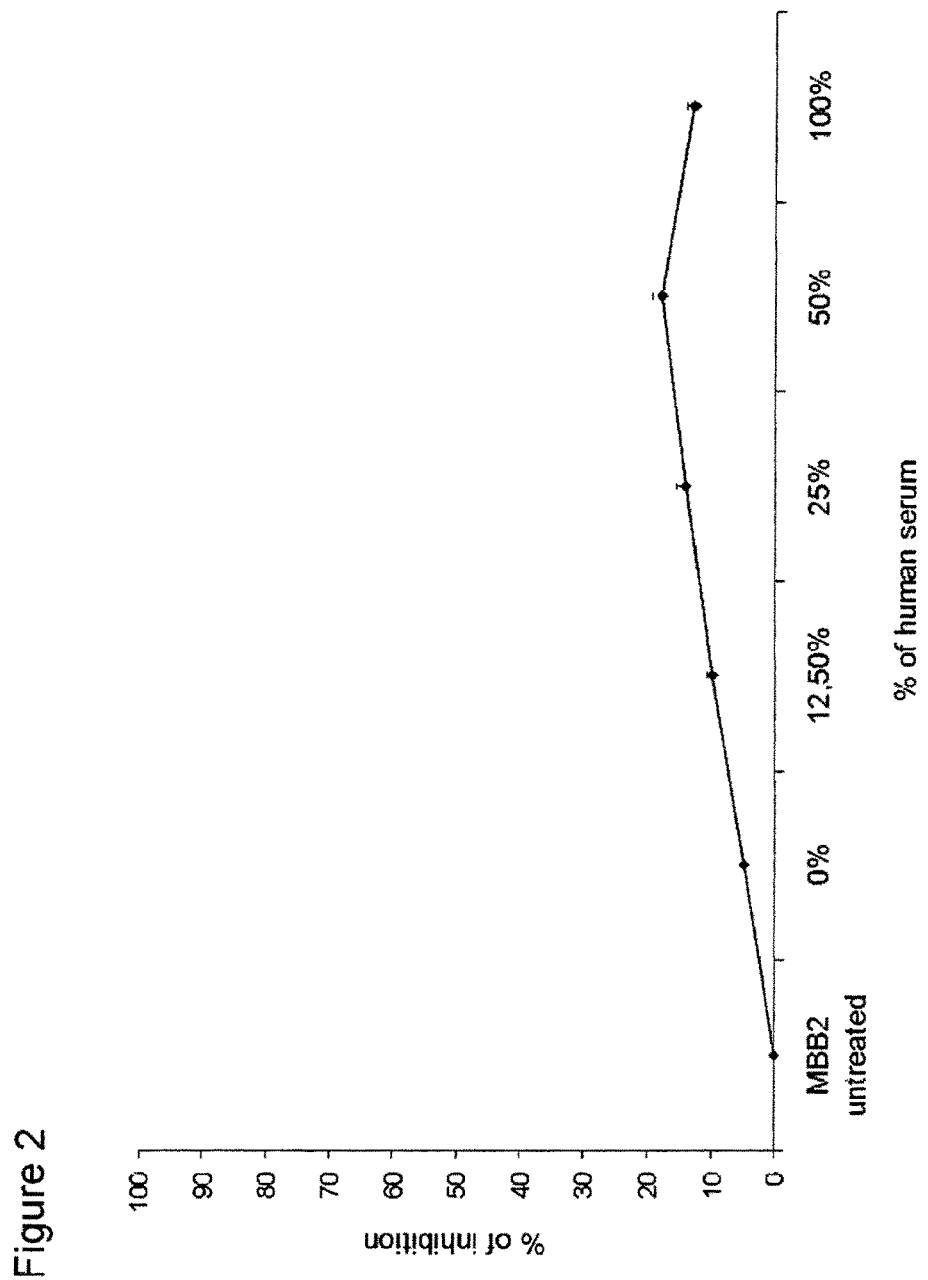
FIG. 2. Analysis of the inhibitory effect of soluble β2GPI on the binding of MBB2 to solid phase bound molecule. MBB2 (100 ng/100 µl) was incubated with increasing percentage of serum for 2 hr at 37° C. and the residual amount of antibody that was still able to bind to immobilized β2GPI was evaluated by ELISA.
Figure 3:
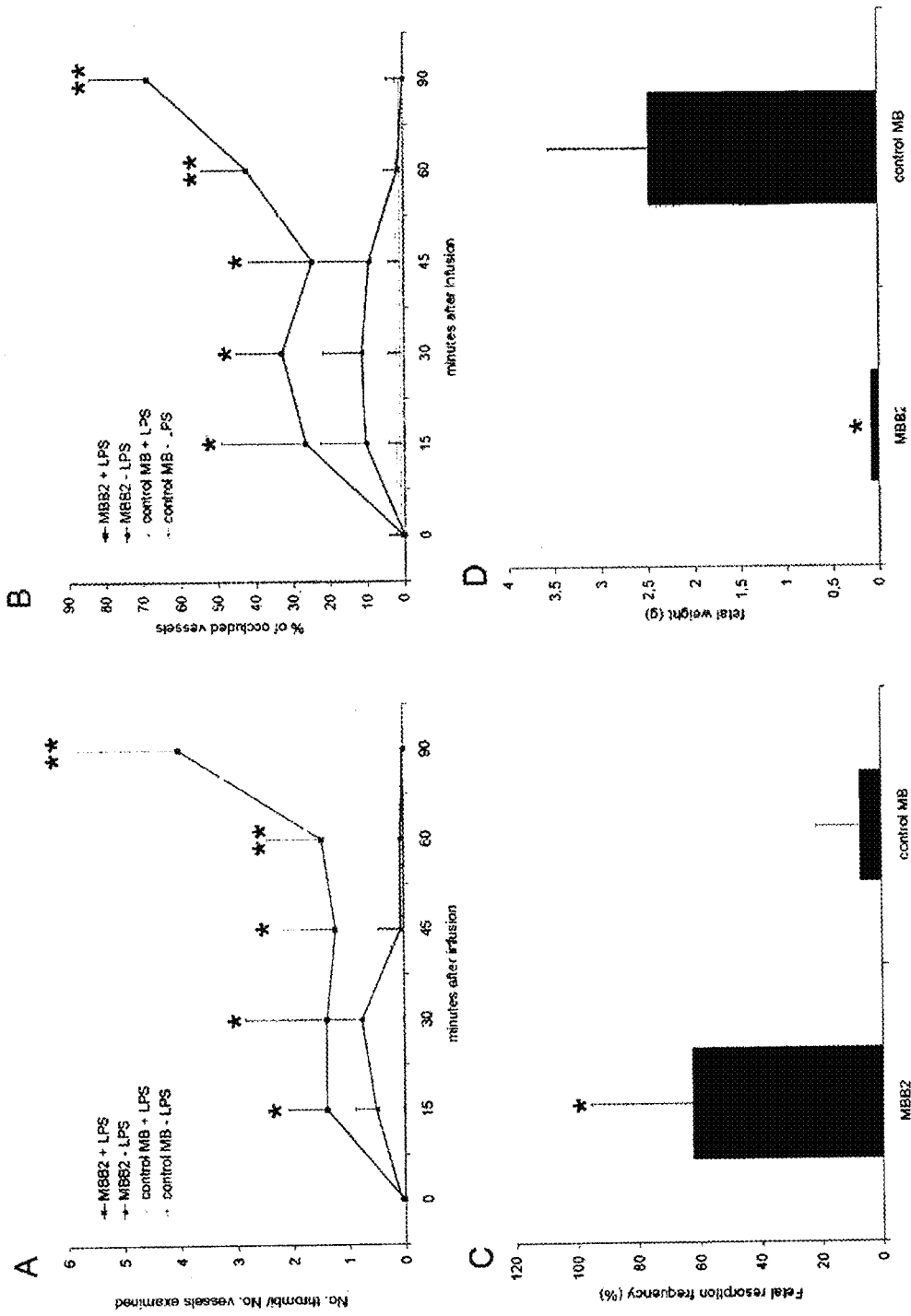
FIG. 3. Analysis of the procoagulant and pro-abortive effects of MBB2. (A) Thrombus formation and (B) vessel occlusion were monitored by intravital microscopy at different time intervals in rats treated or untreated with LPS and perfused with MBB2 or control MB. (C) Percentage of fetal loss and (D) fetal weight in mice treated with MBB2 or control MB. (E) Sections of rat mesenteric tissue showing vessels occlusion with thrombi in LPS treated rats receiving MBB2 and small cell aggregates in MBB2-treated animals in the absence of LPS. Both thrombi and cell aggregates were undetectable in animal treated with control MB. (F) Representative examples of uteri from a MBB2-treated pregnant mouse showing resorbed fetuses indicated with arrows and from unrelated MB-treated mouse containing live pups. The procoagulant effect of the antibodies was evaluated on three rats for each treatment protocol and their pro-abortive activity of MBB2 and control MB was tested on at least 5 pregnant mice for each antibody. The results are expressed as mean± SD. *P<0.05, **P<0.01 versus control MB.
Figure 4:
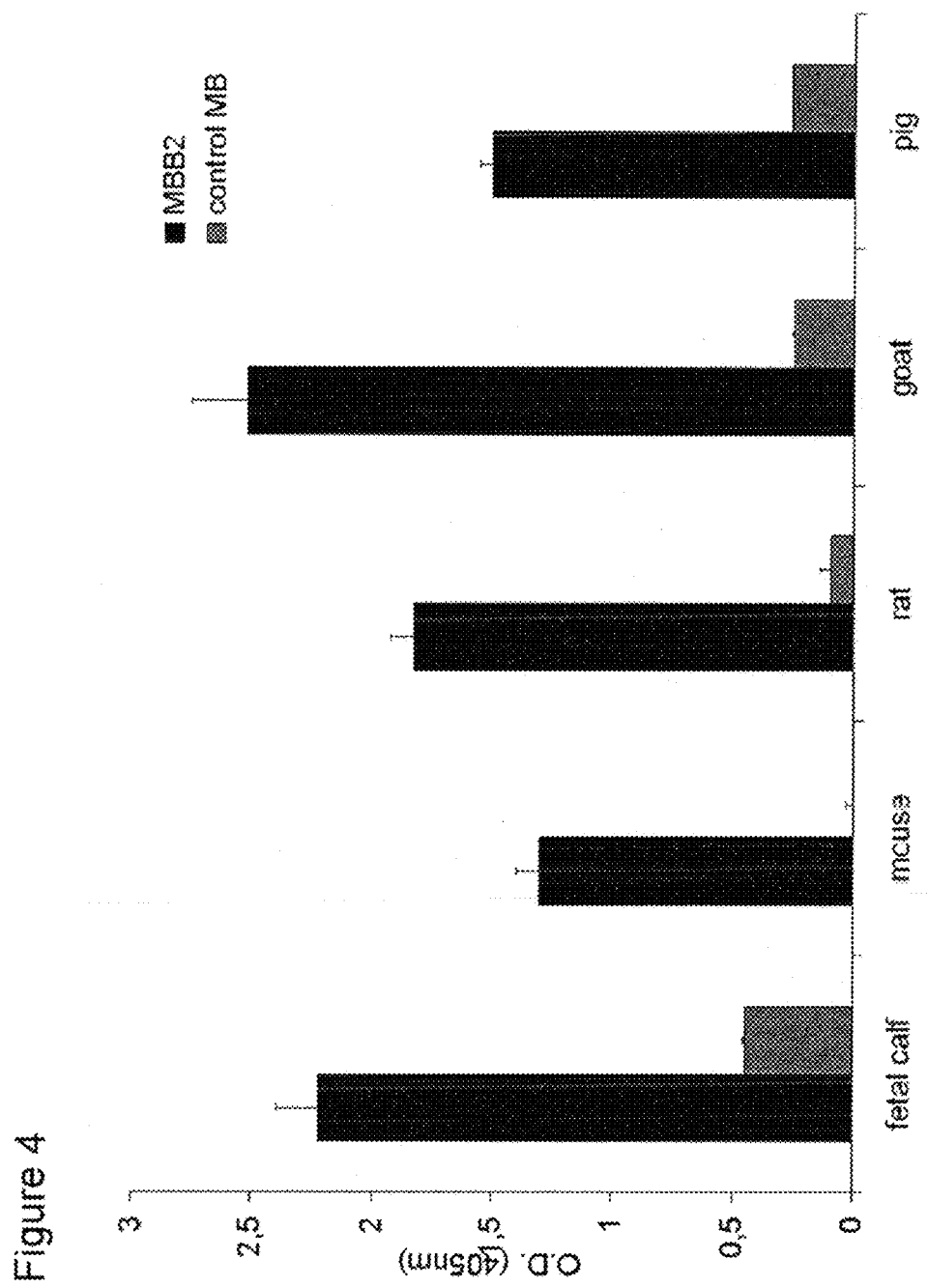
FIG. 4. Recognition of β2GPI from different species by MBB2. Solid-phase bound cardiolipin was incubated with 10% animal sera and then exposed to either MBB2 or control MB. The bound antibody was revealed by ELISA.
Figure 5:
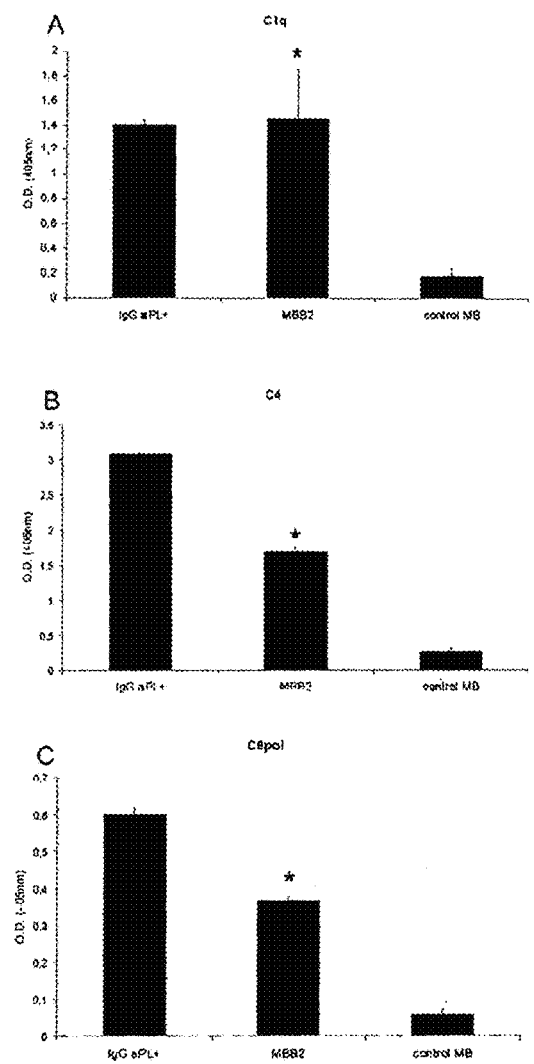
FIG. 5. Complement activation by MBB2. Human β2GPI (10 µg/mL) immobilized on γ-irradiated polystyrene plates was first incubated with MBB2 (1 µg/ml) or with IgG aPL$^+$ from a patient with APS for 90 min at RT and after washing with 1:100 fresh human serum for 30 min at 37° C. Bound C1q, C4 and C9 neoantigen were revealed by ELISA using goat antibodies to C1q and C4 and the monoclonal antibody aE11 to C9 neoantigen. The results of experiments run in triplicates are expressed as mean± SD.
Figure 6:
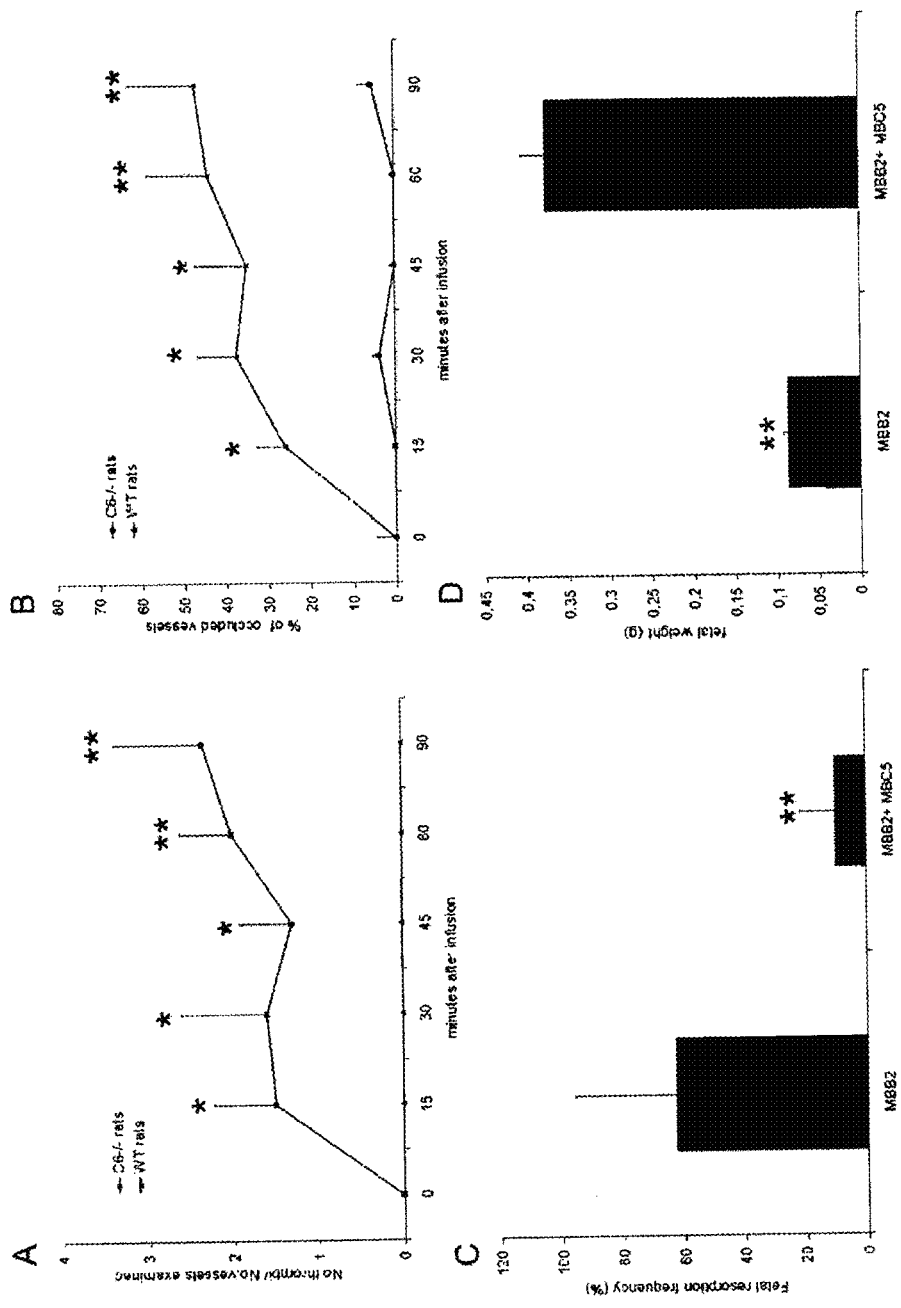
FIG. 6. Analysis of the procoagulant and pro-abortive effect induced by MBB2 in complement-deficient or complement-depleted animals. Thrombus formation (A) and vessel occlusion (B) were monitored by intravital microscopy at different time intervals in LPS-primed C6$^{+/+}$ and C6$^{-/-}$ PVG rats perfused with MBB2. Percentage of fetal loss (C) and fetal weight (D) in normal and C5-depleted mice treated with MBB2. Inununofluorescence analysis of rat mesenteric tissue (E) and fetal implantation sites (F) in normal and complement deficient animals treated with MBB2 for deposition of scFv-Fc, C3 and C9. The procoagulant and the pro-abortive effects of MBB2 were evaluated and expressed as reported in the legend to FIG. 3.
Figure 7:
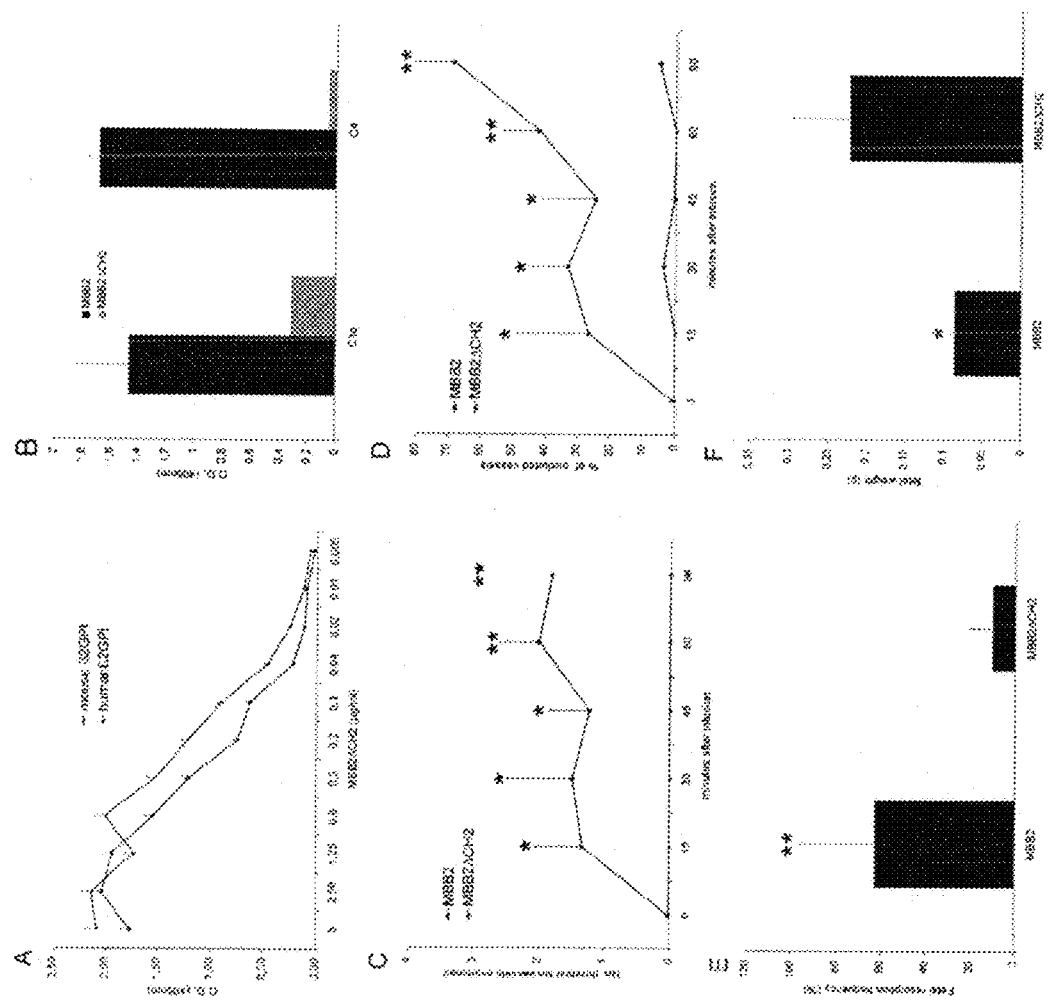
FIG. 7. Binding and in vivo effect of MBB2ΔCH2. Human or mouse β2GPI (10 µg/mL) immobilized on γ-irradiated polystyrene plates were incubated with different concentrations of MBB2 or unrelated MB and the bound minibody was revealed by ELISA (A). Deposition of C1q and C4 to bound MBB2ΔCH2 and MBB2 was evaluated as indicated in the legend of FIG. 5 (B). Thrombus formation (C) and vessel occlusion (D) monitored by intravital microscopy at different time intervals in LPS-primed normal rats perfused with either MBB2ΔCH2 or MBB2. (E) Percentage of fetal loss and (F) fetal weight in pregnant mice treated with either MBB2ΔCH2 or MBB2. The procoagulant and the pro-abortive effects of MBB2 were evaluated and expressed as reported in the legend to FIG. 3.
Figure 8:
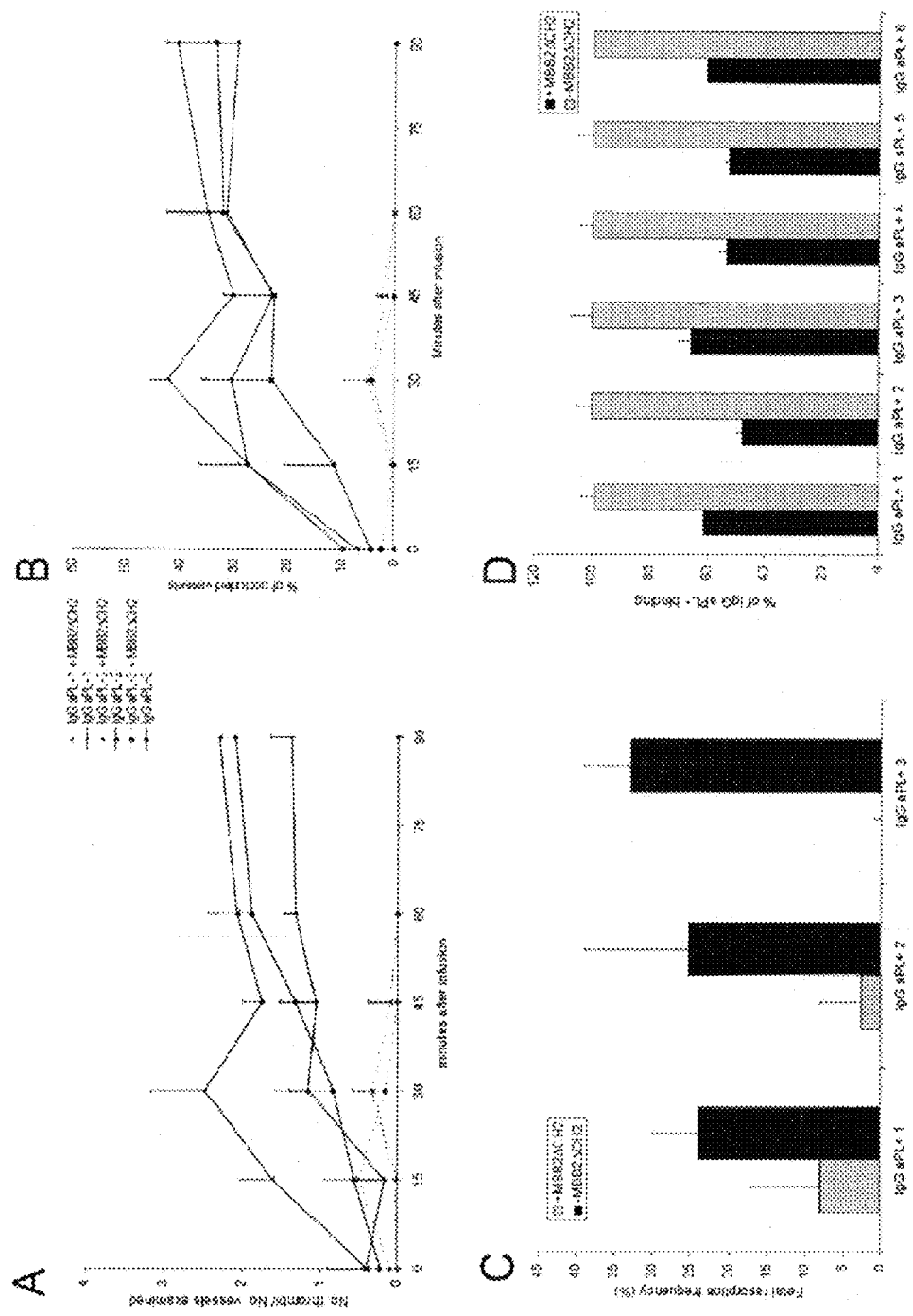
FIG. 8. Control of the pathogenic effect of APL by MBB2ΔCH2.

Thrombus formation (A) and vessel occlusion (B) observed in rats that received IgG (10 mg/ml) purified from 3 APS patients and either MBB2ΔCH2 (2 mg/ml) or control MB. Percentage of fetal loss in pregnant mice receiving patients' IgG and MBB2ΔCH2(C). Displacement of patients' IgG bound to β2GPI by MBB2ΔCH2 evaluated as described in Materials and Methods (D). The procoagulant and the pro-abortive effects of MBB2 were evaluated and expressed as reported in the legend to FIG. 3.

REFERENCES

1. Ruiz-Irastorza, G., Crowther, M., Branch, W. & Khamashta, M. A. Antiphospholipid syndrome. *Lancet* 376, 1498-1509.
2. Erkan, D., Espinosa, G. & Cervera, R. Catastrophic antiphospholipid syndrome: updated diagnostic algorithms. *Autoimmun Rev* 10, 74-79 (2010).
3. Meroni, P. L., et al. Obstetric and vascular APS: same autoantibodies but different diseases? *Lupus* 21, 708-710.
4. McNeil, H. P., Simpson, R. J., Chesterman, C. N. & Krilis, S. A. Anti-phospholipid antibodies are directed against a complex antigen that includes a lipid-binding inhibitor of coagulation: beta 2-glycoprotein I (apolipoprotein H). *Proc Natl Acad Sci USA* 87, 4120-4124 (1990).
5. Galli, M., et al. Anticardiolipin antibodies (ACA) directed not to cardiolipin but to a plasma protein cofactor. *Lancet* 335, 1544-1547 (1990).
6. Matsuura, E., Igarashi, Y., Fujimoto, M., Ichikawa, K. & Koike, T. Anticardiolipin cofactor(s) and differential diagnosis of autoimmune disease. *Lancet* 336, 177-178 (1990).
7. Ioannou, Y. The Michael Mason Prize: Pathogenic antiphospholipid antibodies, stressed out antigens and the deployment of decoys. *Rheumatology (Oxford)* 51, 32-36 (2012).
8. Agostinis, C., et al. In vivo distribution of beta2 glycoprotein I under various pathophysiologic conditions. *Blood* 118, 4231-4238 (2011).
9. Fischetti, F., et al. Thrombus formation induced by antibodies to beta2-glycoprotein I is complement dependent and requires a priming factor. *Blood* 106, 2340-2346 (2005).

10. Meroni, P. L., Borghi, M. O., Raschi, E. & Tedesco, F. Pathogenesis of antiphospholipid syndrome: understanding the antibodies. *Nat Rev Rheumatol* 7, 330-339.
11. Holers, V. M., et al. Complement C3 activation is required for antiphospholipid antibody-induced fetal loss. *J Exp Med* 195, 211-220 (2002).
12. Girardi, G., et al. Complement C5a receptors and neutrophils mediate fetal injury in the antiphospholipid syndrome. *J Clin Invest* 112, 1644-1654 (2003).
13. de Jesus, G. R., et al. Management of obstetric antiphospholipid syndrome. *Curr Rheumatol Rep* 14, 79-86.
14. Ernest, J. M., Marshburn, P. B. & Kutteh, W. H. Obstetric antiphospholipid syndrome: an update on pathophysiology and management. *Semin Reprod Med* 29, 522-539.
15. Empson, M., Lassere, M., Craig, J. & Scott, J. Prevention of recurrent miscarriage for women with antiphospholipid antibody or lupus anticoagulant. *Cochrane Database Syst Rev*, CD002859 (2005).
16. Ioannou, Y., et al. Binding of antiphospholipid antibodies to discontinuous epitopes on domain I of human beta(2)-glycoprotein I: mutation studies including residues R39 to R43. *Arthritis Rheum* 56, 280-290 (2007).
17. Ellinger, I., Schwab, M., Stefanescu, A., Hunziker, W. & Fuchs, R. IgG transport across trophoblast-derived BeWo cells: a model system to study IgG transport in the placenta. *Eur J Immunol* 29, 733-744 (1999).
18. Agar, C., et al. Beta2-glycoprotein I can exist in 2 conformations: implications for our understanding of the antiphospholipid syndrome. *Blood* 116, 1336-1343.
19. Steinkasserer, A., et al. Activity, disulphide mapping and structural modelling of the fifth domain of human beta 2-glycoprotein I. *FEBS Lett* 313, 193-197 (1992).
20. de Groot, P. G. & Derksen, R. H. Pathophysiology of antiphospholipid antibodies. *Neth J Med* 62, 267-272 (2004).
21. de Laat, H. B., Derksen, R. H., Urbanus, R. T., Roest, M. & de Groot, P. G. beta2-glycoprotein I-dependent lupus anticoagulant highly correlates with thrombosis in the antiphospholipid syndrome. *Blood* 104, 3598-3602 (2004).
22. Ritis, K., et al. A novel C5a receptor-tissue factor cross-talk in neutrophils links innate immunity to coagulation pathways. *J Immunol* 177, 4794-4802 (2006).
23. Redecha, P., et al. Tissue factor: a link between C5a and neutrophil activation in antiphospholipid antibody induced fetal injury. *Blood* 110, 2423-2431 (2007).
24. Carrera-Marin, A., et al. C6 knock-out mice are protected from thrombophilia mediated by antiphospholipid antibodies. *Lupus* 21, 1497-1505.
25. Pierangeli, S. S., Vega-Ostertag, M. & Harris, E. N. Intracellular signaling triggered by antiphospholipid antibodies in platelets and endothelial cells: a pathway to targeted therapies. *Thromb Res* 114, 467-476 (2004).
26. Ostertag, M. V., Liu, X., Henderson, V. & Pierangeli, S. S. A peptide that mimics the Vth region of beta-2-glycoprotein I reverses antiphospholipid-mediated thrombosis in mice. *Lupus* 15, 358-365 (2006).
27. de la Torre, Y. M., et al. Anti-phospholipid induced murine fetal loss: novel protective effect of a peptide targeting the beta2 glycoprotein I phospholipid-binding site. Implications for human fetal loss. *J Autoimmun* 38, J209-215.
28. Robertson, J. A. Protecting embryos and burdening women: assisted reproduction in Italy. *Hum Reprod* 19, 1693-1696 (2004).
29. Cavazzana, A., et al. Anti-beta(2)-glycoprotein I ELISA assay: the influence of different antigen preparations. *Thromb Haemost* 101, 789-791 (2009).
30. Sblattero, D. & Bradbury, A. Exploiting recombination in single bacteria to make large phage antibody libraries. *Nat Biotechnol* 18, 75-80 (2000).
31. Di Niro, R., et al. Construction of miniantibodies for the in vivo study of human autoimmune diseases in animal models. *BMC Biotechnol* 7, 46 (2007).
32. Marzari, R., et al. The cleavage site of C5 from man and animals as a common target for neutralizing human monoclonal antibodies: in vitro and in vivo studies. *Eur J Immunol* 32, 2773-2782 (2002).
33. Roovers, R. C., van der Linden, E., de Bruine, A. P., Arends, J. W. & Hoogenboom, H. R. In vitro characterisation of a monovalent and bivalent form of a fully human anti Ep-CAM phage antibody. *Cancer Immunol Immunother* 50, 51-59 (2001).
34. Boscolo, S., et al. Simple scale-up of recombinant antibody production using an UCOE containing vector. *N Biotechnol* 29, 477-484 (2012).
35. Tincani, A. & Meroni, P. L. Anticardiolipin antibodies: to be or not to be detectable. *Clin Exp Rheumatol* 19, 240-241 (2001).
36. Tedesco, F., et al. The cytolytically inactive terminal complement complex activates endothelial cells to express adhesion molecules and tissue factor procoagulant activity. *J Exp Med* 185, 1619-1627 (1997).
37. Leenaerts, P. L., et al. Hereditary C6 deficiency in a strain of PVG/c rats. *Clin Exp Immunol* 97, 478-482 (1994).
38. Steinkasserer, A., Estaller, C., Weiss, E. H., Sim R. B. & Day, A. J. Complete nucleotide and deduced amino acid sequence of human beta 2-glycoprotein I. Biochem. J. 277, 387-391, 1991
39. Iverson G. M., Victoria E. J, and Marquis D M. Anti-b2 glycoprotein I (b2GPI) autoantibodies for the construction of the individual domains I, II, IV and V of b2-GPI recognize an epitope on the first domain of b2GPI *Proc. Natl. Acad. Sci. USA* 95, 15542-15546, 1998
40. Van Os G. M. A,. Meijers J . C. M, Agar C, Seron M. V., . Marquart J. A, Akesson P, Urbanus R. T., Derksen R. H. W. M, Herwald H., Morgelin M and. de Groot P. G- Induction of anti-b2-glycoprotein I autoantibodies in mice by protein H of Streptococcus pyogenes Journal of Thrombosis and Haemostasis, 9: 2447-2456, 2011
41. Ioannou Y., Giles I., Lambrianides A., Richardson C., Pearl L. H., Latchman D. S, Isenberg D. A. and Rahman A. BMC Biotechnology, 6, 8, 2006.

The invention claimed is:

1. A human recombinant antibody binding to β2GPI, wherein said antibody is unable to activate complement and contains VH and VL chains having the sequences SEQ ID NO: 1 and SEQ ID NO:2, respectively.

2. The antibody of claim 1, which binds to the DI domain of β2GPI.

3. The antibody of claim 1, which is an IgG.

4. The antibody of claim 1, the CH2 domain of which is deleted whereby said antibody becomes unable to activate complement.

5. A fragment of the antibody of claim 1, which is selected from scFv and scFv-Fc.

6. The scFv fragment of claim 5, which is encoded by the polynucleotide SEQ ID NO:7.

7. The scFv-Fc fragment of claim 5, which is CH2 domain-deleted.

8. An antibody according to claim 1 or an antibody fragment thereof selected from scFv and scFv-Fc, which is able to displace autoantibodies bound to β2GPI from patients affected by antiphospholipid syndrome (APS), in in vitro competitive binding assays.

9. A pharmaceutical composition comprising, as an active ingredient, an antibody of claim 1 or an antibody fragment thereof selected from scFv and scFv-Fc, and a pharmaceutically acceptable carrier.

10. Method of treating thrombus formation, vessel occlusion or fetal loss in patients affected by antiphospholipid syndrome (APS) in patients in need thereof, said method comprising administering to said patients an effective amount of an antibody according to claim 1 or an antibody fragment thereof selected from scFv and scFv-Fc or a pharmaceutical composition comprising said antibody or said antibody fragment; and treating said thrombus formation, said vessel occlusion or said fetal loss in said patients.

\* \* \* \* \*